US006849253B2

(12) United States Patent
Chowhan et al.

(10) Patent No.: US 6,849,253 B2
(45) Date of Patent: *Feb. 1, 2005

(54) USE OF BORATE-POLYOL COMPLEXES IN OPHTHALMIC COMPOSITIONS

(75) Inventors: Masood Chowhan, Arlington, TX (US); Nissanke L. Dassanayake, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/302,294

(22) Filed: Nov. 22, 2002

(65) Prior Publication Data

US 2003/0130207 A1 Jul. 10, 2003

Related U.S. Application Data

(63) Continuation of application No. 10/027,998, filed on Dec. 19, 2001, now Pat. No. 6,503,497, which is a continuation of application No. 09/597,310, filed on Jun. 20, 2000, now Pat. No. 6,365,636, which is a continuation of application No. 09/109,453, filed on Jul. 2, 1998, now Pat. No. 6,143,799, which is a division of application No. 08/479,281, filed on Jun. 7, 1995, now Pat. No. 5,811,466, which is a division of application No. 08/198,427, filed on Feb. 22, 1994, now Pat. No. 5,505,953, which is a continuation-in-part of application No. 08/118,833, filed on Sep. 7, 1993, now Pat. No. 5,342,620, which is a continuation of application No. 07/879,435, filed on May 6, 1992, now abandoned.

(51) Int. Cl.$^7$ ............................ A61K 9/00; A61K 9/08
(52) U.S. Cl. .................... 424/78.04; 424/427; 514/912; 514/839; 514/840; 514/812; 514/254
(58) Field of Search .......................... 424/78.04, 427; 424/78.26, 659; 514/912, 839, 840, 812, 254

(56) References Cited

U.S. PATENT DOCUMENTS

| 3,975,536 | A | 8/1976 | Stevenson et al. |
| 4,029,817 | A | 6/1977 | Blanco et al. |
| 4,053,628 | A | 10/1977 | Stevenson et al. |
| 4,410,442 | A | 10/1983 | Lucas et al. |
| 4,525,346 | A | 6/1985 | Stark |
| 4,559,186 | A | 12/1985 | Lee |
| 4,581,379 | A | 4/1986 | Nelson et al. |
| 4,675,184 | A | 6/1987 | Hasegawa et al. |
| 4,710,313 | A | 12/1987 | Miyajima et al. |
| 4,748,189 | A | 5/1988 | Su et al. |
| 4,758,595 | A | 7/1988 | Ogunbiyi et al. |
| 4,780,465 | A | 10/1988 | Ogata et al. |
| 4,820,352 | A | 4/1989 | Riedhammer |
| 4,960,799 | A | 10/1990 | Nagy |
| 5,011,661 | A | 4/1991 | Schäfer |
| 5,032,392 | A | 7/1991 | Varma |
| 5,141,665 | A | 8/1992 | Sherman |
| 5,171,526 | A | 12/1992 | Wong et al. |
| 5,188,826 | A | 2/1993 | Chandrasekaran |
| 5,281,277 | A | 1/1994 | Nakagawa et al. |
| 5,342,620 | A | 8/1994 | Chowhan |
| 5,460,658 | A | 10/1995 | Nakagawa et al. |
| 5,494,937 | A | 2/1996 | Asgharian et al. |
| 5,505,953 | A | 4/1996 | Chowhan et al. |
| 5,576,278 | A | 11/1996 | Van Duzee et al. |
| 5,604,190 | A | 2/1997 | Chowhan et al. |
| 5,653,972 | A | 8/1997 | Desai et al. |
| 5,672,213 | A | 9/1997 | Asgharian et al. |
| 5,811,466 | A | 9/1998 | Chowhan et al. |
| 6,143,799 | A | 11/2000 | Chowhan et al. |
| 6,184,189 | B1 | 2/2001 | Asgharian et al. |
| 6,365,636 | B1 | 4/2002 | Chowhan et al. |
| 6,503,497 | B2 * | 1/2003 | Chowhan et al. ......... 424/78.04 |

FOREIGN PATENT DOCUMENTS

| EP | 0 109 561 A1 | 5/1984 |
| EP | 0 436 726 A1 | 7/1991 |
| FR | 2.230.358 | 12/1974 |
| GB | 2016446 | 9/1979 |
| WO | WO 93/02663 | 2/1993 |
| WO | WO 93/21903 | 11/1993 |

OTHER PUBLICATIONS

*Chemical Abstracts*, vol. 101 (1984): 86888j, Hentschell, et al., "Agent to preserve bacterialogical specimens".
*Chemical Abstracts*, vol. 94 (1981): 135600g. Opus Chemical AB, "Borane complexes as bacterial preservatives".
Gilman, H. et al. (eds), "Organic Chemistry" vol. II, John Wiley & Sons, Inc., New York, pp. 1606–1610 (1950).
Morawetz, H., "Macromolecules in Solution", John Wiley & Sons, Inc., New York, pp 402–404 (1974).
Okada, T. I., *Chromatography*, 403:27–33 (1987).
Rakow, P.L., *Contact Lens Forum*, pp 41–46 (Jun., 1988).
*Remington's Pharmaceutical Sciences*, Mack Publishing Company, Easton, PA, p. 1445 (1980).
Sciarra, J., et al., *J. Am. Pharm. Assoc.*, 49(2):115–117 (1960).

* cited by examiner

*Primary Examiner*—Gary Kunz
*Assistant Examiner*—Mina Haghighatian
(74) *Attorney, Agent, or Firm*—Gregg C. Brown

(57) ABSTRACT

Water-soluble borate-polyol complexes are useful as buffers and/or antimicrobials in aqueous ophthalmic compositions, including those containing polyvinyl alcohol. These compositions have greater antimicrobial activity than comparable compositions containing typical borate buffers and unexpectedly increase the antimicrobial efficacy of other antimicrobial agents when used in combination. In addition, use of the borate-polyol complexes avoids the incompatibility problem typically associated with the combination of borate buffer and polyvinyl alcohol; therefore, the compositions disclosed herein may also contain polyvinyl alcohol.

18 Claims, No Drawings

USE OF BORATE-POLYOL COMPLEXES IN OPHTHALMIC COMPOSITIONS

CROSS-REFERENCE TO RELATED APPLICATIONS

The present application is a continuation of U.S. patent application Ser. No. 10/027,998, filed Dec. 19, 2001 (now U.S. Pat. No. 6,503,497), which is a continuation of U.S. patent application Ser. No. 09/597,310, filed Jun. 20, 2000 (now U.S. Pat. No. 6,365,636), which is a continuation of U.S. patent application Ser. No. 09/109,453, filed Jul. 2, 1998 (now U.S. Pat. No. 6,143,799), which is a divisional of U.S. patent application Ser. No. 08/479,281, filed May 7, 1995 (now U.S. Pat. No. 5,811,466), which is a divisional of U.S. patent application Ser. No. 08/198,427, filed Feb. 22, 1994 (now U.S. Pat. No. 5,505,953), which is a continuation-in-part of U.S. patent application Ser. No. 08/118,833, filed Sep. 17, 1993 (now U.S. Pat. No. 5,342,620), which is a continuation of U.S. patent application Ser. No. 07/879,435, filed May 6, 1992 (now abandoned).

BACKGROUND OF THE INVENTION

This invention relates to the use of borate-polyol complexes in ophthalmic compositions. In particular, these complexes are useful as buffers and/or antimicrobial agents in aqueous ophthalmic compositions, including those ophthalmic compositions containing polyvinyl alcohol.

Ophthalmic compositions are generally formulated to have a pH between about 4.0 and 8.0. To achieve a pH in this range and to maintain the pH for optimal stability during the shelf life of the composition, a buffer is often included. Borate is the buffer of choice for use in ophthalmic compositions, since it has some inherent antimicrobial activity and often enhances the activity of antimicrobials; however, when polyvinyl alcohol (PVA) is also an ingredient in the composition, borate and PVA form a water-insoluble complex which precipitates out of solution and acts as an irritant in the eye. This incompatibility of borate and PVA in contact lens solutions is well-known, and has been discussed, for example, in an article by P. L. Rakow in *Contact Lens Forum*, (June 1988), pages 41–46. Moreover, borate buffer cannot be effectively used below pH 7.0 due to its low buffering capacity to lower pH.

Since borate is incompatible with PVA, ophthalmic compositions containing PVA are generally buffered with acetate, phosphate or other buffers. There are disadvantages to using these alternative buffers: for example, acetate is a weak buffer ($pK_a$ of about 4.5), so a relatively large amount is needed; on the other hand, phosphate is a good buffer but, when used in concentrations generally found in ophthalmic formulations, it reduces the antimicrobial activity of preservatives.

It is well known that small organic compounds, such as benzalkonium chloride (BAC), chlorhexidine, thimerosal have excellent antimicrobial activity; however, it is now known that these small organic antimicrobials are often toxic to the sensitive tissues of the eye and can accumulate in contact lenses, particularly soft, hydrophilic contact lenses. More recently, polymeric antimicrobials such as Polyquad® (polyquaternium-1) and Dymed® (polyhexamethylene biguanide) have been used in contact lens care products as disinfectants and preservatives. While these polymeric antimicrobials exhibit a broad spectrum of antimicrobial activity, they generally have relatively weak antifungal activity, especially against *Aspergillus niger* and *Aspergillus fumigatus*.

A need therefore exists for ophthalmic compositions which have an optimal pH for stability and efficacy, but whose antimicrobial efficacy is not compromised.

SUMMARY OF THE INVENTION

This invention provides such ophthalmic compositions. The ophthalmic compositions of the present invention comprise borate-polyol complexes which have surprisingly been found to have increased antimicrobial activity as compared to boric acid or its salts, particularly with respect to organisms such as *A. niger*. Moreover, these complexes unexpectedly increase the antimicrobial efficacy of other antimicrobial agents when used in combination.

The borate-polyol complexes are formed by mixing boric acid and/or its salts with polyols, such as mannitol, glycerin or propylene glycol, in an aqueous solution. The resultant solution may then be used as a buffer and/or antimicrobial agent in aqueous ophthalmic compositions, even where such compositions also contain PVA. The borate-polyol complexes of the present invention are also useful in unpreserved saline solutions.

The borate-polyol complexes of the present invention are particularly useful as adjunctive disinfecting agents in contact lens disinfecting solutions containing monomeric quaternary ammonium compounds (e.g., benzalkonium chloride) or biguanides (e.g., chlorhexidine) or polymeric antimicrobials, such as polymeric quaternary ammonium compounds (e.g., Polyquad®, Alcon Laboratories, Inc., Fort Worth, Tex.) or polymeric biguanides (e.g., Dymed®, Bausch & Lomb, Rochester, N.Y.).

The compositions of the present invention may optionally contain PVA; such compositions are particularly useful in contact lens care products which are targeted for wearers of rigid gas-permeable contact lenses (RGPs), who often complain of discomfort. PVA is a viscosity enhancer and is used extensively in all types of RGP products in order to improve the comfort and wearing time of RGPs. PVA is also extensively used as a viscosity enhancer for pharmaceutical ophthalmic compositions such as eye drops, gels or ocular inserts.

DETAILED DESCRIPTION OF THE INVENTION

As used herein, the term "borate" shall refer to boric acid, salts of boric acid and other pharmaceutically acceptable borates, or combinations thereof. Most suitable are: boric acid, sodium borate, potassium borate, calcium borate, magnesium borate, manganese borate, and other such borate salts.

As used herein, and unless otherwise indicated, the term "polyol" shall refer to any compound having at least two adjacent —OH groups which are not in trans configuration relative to each other. The polyols can be linear or circular, substituted or unsubstituted, or mixtures thereof, so long as the resultant complex is water-soluble and pharmaceutically acceptable. Such compounds include sugars, sugar alcohols, sugar acids and uronic acids. Preferred polyols are sugars, sugar alcohols and sugar acids, including, but not limited to: mannitol, glycerin, propylene glycol and sorbitol. Especially preferred polyols are mannitol and glycerin; most preferred is mannitol.

The water-soluble borate-polyol complexes of the present invention may be formed by mixing borate with the polyol (s) of choice in an aqueous solution. These complexes can be used in conjunction with other known preservatives and disinfectants to meet preservative efficacy and disinfection standards. In such compositions, the molar ratio of borate to polyol is generally between about 1:1 and about 1:10, and is preferably between about 1:1 and about 1:2.5.

The borate-polyol complexes may also be used in unpreserved salines to meet preservative efficacy standards. In these unpreserved salines, the molar ratio of borate to polyol is generally between about 1:0.1 and about 1:1, and is especially between about 1:0.25 and about 1:0.75. Some borate-polyol complexes, such as potassium borotartrate, are commercially available.

The borate-polyol complexes are utilized in the compositions of the present invention in an amount between about 0.5 to about 6.0 percent by weight (wt %), preferably between about 1.0 to about 2.5 wt %. The optimum amount, however, will depend upon the complexity of the product, since potential interactions may occur with the other components of a composition. Such optimum amount can be readily determined by one skilled in the formulatory arts.

The compositions of the present invention useful with RGPs or compositions such as eye drops, gels or ocular inserts will preferably also contain PVA or other viscosity-enhancing polymers, such as cellulosic polymers or carboxy vinyl polymers. PVA is available in a number of grades, each differing in degree of polymerization, percent of hydrolysis, and residual acetate content. Such differences affect the physical and chemical behavior of the different grades. PVA can be divided into two broad categories, i.e., completely hydrolyzed and partially hydrolyzed. Those containing 4% residual acetate content or less are referred to as completely hydrolyzed. Partially hydrolyzed grades usually contain 20% or more residual acetate. The molecular weight of PVA's lo vary from 20,000 to 200,000. In general, PVA used in ophthalmic products has an average molecular weight in the range of 30,000 to 100,000 with 11% to 15% residual acetate. Compositions of the present invention generally contain such types of PVA at a concentration less than about 10.0 wt %, preferably between about 0.1 and about 1.4 wt % and most preferably at a concentration of about 0.75 wt %.

EXAMPLE 1

The water-soluble borate-polyol complexes of the present invention may be prepared as illustrated below.

| INGREDIENT | FORMULATION (% weight/volume) | | | | | | | |
| --- | --- | --- | --- | --- | --- | --- | --- | --- |
| | A | B | C | D | E | F | G | H |
| Boric acid | 0.35 | 0.35 | 0.35 | 0.35 | 0.35 | 0.35 | 0.35 | 0.35 |
| Sodium borate | 0.11 | 0.11 | 0.11 | 0.11 | 0.11 | 0.11 | 0.11 | 0.11 |
| Mannitol | 0.5 | 1.0 | 1.5 | 2.0 | — | — | — | — |
| Glycerin | — | — | — | — | 0.5 | 1.0 | 1.5 | 2.0 |
| Na$_2$EDTA | 0.1 | 0.1 | 0.1 | 0.1 | 0.1 | 0.1 | 0.1 | 0.1 |
| Purified water | q.s. | q.s. | q.s. | q.s. | q.s. | q.s. | q.s. | q.s. |
| HCl/NaOH | pH 7.4 | pH 7.4 | pH 7.4 | pH 7.4 | pH 7.4 | pH 7.4 | pH 7.4 | pH 7.4 |
| Polyquad ® | 0.001+ 10% xs | 0.001+ 10% xs | 0.001+ 10% xs | 0.001+ 10% xs | 0.001+ 10% xs | 0.001+ 10% xs | 0.001+ 10% xs | 0.001+ 10% xs |

Preparation:

Formulations A–H were prepared as follows. Tubular, labeled and calibrated 150 milliliter (mL) beakers were each filled with about 90 mL of purified water. Boric acid, sodium borate and mannitol or glycerin were then added and dissolved by stirring the solution for about 25 minutes. At this time, disodium EDTA (ethylene diamine tetraacetic acid) was added with stirring. Purified water was added to bring the solutions almost to 100% (100 mL), pH was adjusted to approximately 7.4 and the osmolality was measured. Polyquad® was then added and the volume brought to 100% by the addition of purified water. pH was again measured and adjusted, if necessary, and the osmolality was measured again.

It is not always necessary to have an isotonic solution; however, if there is a need to have an isotonic solution, the osmolality can be adjusted by incorporating polyol with OH groups in trans position, sodium chloride, potassium chloride, calcium chloride or is other osmolality building agents which are generally acceptable in ophthalmic formulations and known to those skilled in the art.

EXAMPLE 2

Aqueous ophthalmic compositions of the present invention may be prepared using the formulations illustrated below.

| | FORMULATION (percent by weight) | | | | | | | | |
|---|---|---|---|---|---|---|---|---|---|
| INGREDIENT | 1 | 2 | 3 | 4 | 5 | 6 | 7 | 8 | 9 |
| PVA | 0.75 | 1.4 | 0.75 | 0.75 | 0.75 | 0.75 | 0.75 | 0.75 | 0.75 |
| Hydroxyethyl cellulose (HEC) | — | — | 0.75 | 0.28 | 0.28 | 0.28 | 0.28 | 0.75 | 0.75 |
| Mannitol | 2.0 | 2.0 | 2.0 | 2.0 | 2.0 | 2.0 | 0.5 | 2.0 | 2.0 |
| Boric acid | 0.35 | 0.35 | 0.35 | 0.35 | 0.35 | 0.35 | 0.35 | 0.35 | 0.35 |
| Sodium borate | 0.11 | 0.11 | 0.11 | 0.11 | 0.11 | 0.11 | 0.11 | 0.11 | 0.11 |
| Edetate disodium | 0.1 | 0.1 | 0.1 | 0.1 | 0.1 | 0.1 | 0.1 | 0.1 | 0.1 |
| Sodium chloride | 0.09 | 0.09 | 0.09 | 0.09 | 0.45 | 0.09 | 0.09 | 0.09 | 0.09 |
| Polyquad ® | 0.001 | 0.001 | 0.001 | 0.001 | 0.001 | 0.001 | 0.001 | — | — |
| Sucrose | — | — | — | — | — | 2.5 | — | 2.5 | 2.5 |
| Polyhexamethylene biguanide | — | — | — | — | — | — | — | 0.0005 | — |
| BAC | — | — | — | — | — | — | — | — | 0.004 |

Preparation:

Formulations 1–9 were prepared as follows. A first solution (Solution A) was prepared by adding 500 mL of warm purified water to a calibrated two liter aspirator bottle equipped with a magnetic stirrer. PVA and hydroxyethyl cellulose were then added to Solution A and the contents dispersed by stirring. After dispersal of the polymers, a filter assembly was attached to the aspirator bottle (142 mm Millipore filter holder with 0.2 i filter), and this whole apparatus autoclaved at 121° C. for 30 minutes. Solution A with the filter assembly attached was then allowed to cool to room temperature with stirring. A second solution (Solution B), was prepared in a 500 mL beaker containing 300 mL of purified water by adding boric acid, sodium borate and mannitol and dissolving the contents by stirring for 25 minutes. Edetate disodium, sodium chloride, preservatives and other osmolality-building agents, as necessary, were added to Solution B and the contents dissolved with stirring. Solution B was then sterile filtered into the aspirator bottle containing Solution A. The pH of the resultant solution was then adjusted and the volume brought to 100% by sterile filtering purified water.

EXAMPLE 3

The following ophthalmic compositions of the present invention may also be prepared using the procedure detailed in Example 2.

| | FORMULATION (percent by weight) | | | | | | | | | |
|---|---|---|---|---|---|---|---|---|---|---|
| INGREDIENT | 10 | 11 | 12 | 13 | 14 | 15 | 16 | 17 | 18 | 19 |
| PVA | 1.4 | 1.4 | 1.4 | 1.4 | 1.4 | 1.4 | 1.4 | 1.4 | 1.4 | 1.4 |
| Naphazolene HCl | 0.1 | 0.1 | — | — | — | — | — | — | — | — |
| Sodium sulfacetamide | — | — | — | 10.0 | — | — | — | — | — | — |
| Fluorometholone | — | — | — | — | 0.1 | — | — | — | — | — |
| Gentamycin sulfate | — | — | — | — | — | 0.4 | — | — | — | — |
| Levobunolol HCl | — | — | 0.5 | — | — | — | — | — | — | — |
| Mydrysone | — | — | — | — | — | — | 1.0 | — | — | — |
| Pilocarpine nitrate | — | — | — | — | — | — | — | 1.0 | 1.0 | 1.0 |
| Sodium metabisulfite | — | — | 0.4 | — | — | — | — | — | — | — |
| Mannitol | 2.0 | 2.0 | 2.0 | 2.0 | 2.0 | 2.0 | 2.0 | 2.0 | 4.0 | 0.5 |
| Boric acid | 0.35 | 0.35 | 0.35 | 0.35 | 0.35 | 0.35 | 0.35 | 0.35 | 0.35 | 0.5 |
| Sodium borate | 0.11 | 0.11 | 0.11 | 0.11 | 0.11 | 0.11 | 0.11 | 0.11 | — | — |
| Sodium chloride | 0.45 | 0.45 | 0.45 | — | 0.45 | 0.45 | 0.45 | 0.45 | — | — |
| Edetate disodium | 0.1 | 0.1 | 0.1 | 0.1 | 0.1 | 0.1 | 0.1 | 0.1 | 0.1 | 0.1 |
| BAC | 0.004 | — | — | — | — | — | — | — | — | — |
| Polyquad ® | — | 0.001 | 0.001 | 0.001 | 0.001 | 0.001 | 0.001 | 0.001 | 0.001 | 0.001 |

EXAMPLE 4

The following is a typical wetting and soaking composition of the present invention for use with RGPs.

| INGREDIENT | AMOUNT (wt %) |
|---|---|
| PVA | 0.75 |
| HEC | 0.38 |
| Boric acid | 0.35 |
| Sodium borate | 0.11 |

-continued

| INGREDIENT | AMOUNT (wt %) |
| --- | --- |
| Mannitol | 2.0 |
| Potassium chloride | 0.038 |
| Magnesium chloride | 0.02 |
| Calcium chloride | 0.0154 |
| Sodium chloride | 0.09 |
| Polysorbate 80 | 0.005 |
| Polyquad ® | 0.001 |
| NaOH and/or HCl | pH 7.4 |
| Purified water | q.s. |

Preparation:

In a suitable container containing approximately 30% of the final volume of purified water, PVA and HEC were added and dispersed. This solution was then autoclaved. The solution was allowed to cool to room temperature with stirring. In a separate container, containing approximately 50% of the final volume of purified water, boric acid and sodium borate were added, and dissolved, followed by mannitol. This second solution was then stirred for about 30 minutes, then potassim chloride, calcium is chloride, magnesium chloride, sodium chloride, polysorbate 80 and Polyquad® were added, with stirring. The second solution was then added to the first solution via a 0.2 ì filter. Last, the pH was adjusted to 7.4 and the volume brought to 100% with purified water.

EXAMPLE 5

The following is a typical daily cleaner composition of the present invention for use with RGPs and may be prepared in a manner similar to that detailed in Example 4.

| INGREDIENT | AMOUNT (wt %) |
| --- | --- |
| Nylon 1111 | 2.50 |
| Dextran 70 | 6.0 |
| Sodium borate | 0.25 |
| Boric acid | 0.50 |
| Miracare ® 2MCA | 0.50 |
| PDMA-1 | 0.15 |
| Propylene glycol | 10.0 |
| Polyquad ® | 0.0055 |
| EDTA | 0.10 |
| Mannitol | 1.20 |
| NaOH and/or HCl | pH 7.4 |
| Purified water | q.s. |

EXAMPLE 6

The following is a typical wetting and soaking composition of the present invention which may be prepared in a manner similar to that detailed in Example 4.

| INGREDIENT | AMOUNT (wt %) |
| --- | --- |
| Hydroxypropyl methylcellulose (Methocel ® E4M) | 0.72 |
| Mannitol | 1.0 |
| Sodium borate | 0.11 |
| Boric acid | 0.35 |

-continued

| INGREDIENT | AMOUNT (wt %) |
| --- | --- |
| Sodium chloride | 0.19 |
| Polyquad ® | 0.0011 |
| EDTA | 0.10 |
| NaOH and/or HCl | pH 7.4 |
| Purified water | q.s. |

EXAMPLE 7

The following is a typical comfort drop composition of the present invention which may be prepared in a manner similar to that detailed in Example 4.

| INGREDIENT | AMOUNT (w/v %) |
| --- | --- |
| PVA | 0.75 |
| HEC | 0.28 |
| Mannitol | 2.0 |
| Sodium borate | 0.11 |
| Boric acid | 0.35 |
| Sodium chloride | 0.152 |
| Polyquad ® | 0.00082 |
| EDTA | 0.10 |
| NaOH and/or HCl | pH 7.4 |
| Purified water | q.s. |

EXAMPLE 8

The following is a typical RGP cleaner composition of the present invention which may be prepared in a manner similar to that detailed in Example 4.

| INGREDIENT | AMOUNT (wt %) |
| --- | --- |
| French Naturelle ® ES (Nylon 11) | 2.5 |
| Hydroxyethyl cellulose | 0.4 |
| Sodium borate, decahydrate | 0.25 |
| Boric acid | 0.50 |
| Mannitol | 3.5 |
| Miracare ® 2MCA) | 0.50 |
| Isopropyl alcohol (v/v) | 10.0 |
| NaOH and/or HCl | q.s. 7.4 |
| Purified water | q.s. |

EXAMPLE 9

The following is a typical RGP wetting and/or soaking composition of the present invention, which may be prepared in a manner similar to that detailed in Example 4.

| INGREDIENT | AMOUNT (wt %) |
| --- | --- |
| Methocel ® E4M | 0.85 |
| Mannitol | 2.00 |
| Sodium borate | 0.11 |
| Boric acid | 0.35 |
| Sodium chloride | 0.19 |
| Disodium edetate | 0.1 |
| Polyquad ® | 0.001 |

-continued

| INGREDIENT | AMOUNT (wt %) |
|---|---|
| NaOH and/or HCl | pH 7.4 |
| Purified water | q.s. |

EXAMPLE 10

The following study compared the antimicrobial preservative efficacy of two wetting, soaking and disinfecting solutions: one containing phosphate buffer (Formulation A); and the other containing a borate-polyol complex of the present invention (Formulation B).

Formulations A and B are shown in the following table.

| | FORMULATION (wt %) | |
|---|---|---|
| INGREDIENT | A | B |
| PVA | 0.75 | 0.75 |
| HEC | 0.5 | 0.5 |
| Sodium phosphate | 0.67 | — |
| Sodium biophosphate | 0.017 | — |
| Boric acid | — | 0.35 |
| Sodium borate | — | 0.11 |
| Mannitol | — | 2.0 |
| Disodium edetate | 0.1 | 0.1 |
| Sodium chloride | 0.458 | 0.153 |
| Polysorbate 80 | 0.005 | 0.005 |
| Benzalkonium chloride | 0.01 | 0.01 |
| Purified water | q.s. | q.s. |

Formulations A and B were tested against FDA challenge organisms. The log reductions after 1 hour are tabulated below:

| | FORMULATION (log reduction) | |
|---|---|---|
| TEST ORGANISM | A | B |
| A. niger | 2.1 | 4.4 |
| B. albicans | 4.0 | 5.3 |
| P. aeruginosa | 5.3 | 5.3 |
| S. aureus | 5.5 | 5.2 |
| E. coli | 5.5 | 5.5 |

The results shown above indicate that Formulation B (containing borate-polyol complex) has a broader spectrum of activity than Formulation A (containing phosphate buffer), and has greater activity against certain organisms, such as *A. niger*.

EXAMPLE 11

The following study compared the antimicrobial preservative efficacy of two unpreserved saline solutions identical except that one contained a borate-polyol complex of the present invention (Formulation C) and the other contained the conventional borate buffer (Formulation D).

An organism challenge approach based on the British Pharmacopoeia ("BP") 1988 Test for Efficacy of Preservatives in Pharmaceutical Products was used to evaluate the antimicrobial preservative efficacy of Formulations C and D. Formulation samples were inoculated with known levels of *A. niger* and sampled at predetermined intervals to determine if the system was capable of killing or inhibiting the propagation of organisms introduced into the products.

| | FORMULATION (wt %) | |
|---|---|---|
| INGREDIENT | C | D |
| Boric acid | 1.0 | 1.0 |
| Sodium borate | 0.2 | 0.2 |
| Mannitol | 1.5 | — |
| Sodium chloride | — | 0.3 |
| Disodium edetate | 0.1 | 0.1 |
| NaOH and/or HCl | pH 7.4 | pH 7.4 |
| Purified water | q.s. | q.s. |

The results indicated that there was a 3.1 log reduction of *A. niger* with Formulation C and only 1.2 log reduction with Formulation D after 7 days. Formulation C met the BP standards for preservative efficacy against *A. niger*, while Formulation D failed to meet the BP standards.

EXAMPLE 12

The following study compared the antimicrobial preservative efficacy of two disinfecting solutions identical except that one contained a borate-polyol complex of the present invention (Formulation E) and the other contained the conventional borate buffer (Formulation F).

An organism challenge approach based on the BP 1988 Test for Efficacy of Preservatives in Pharmaceutical Products was used to evaluate the antimicrobial preservative efficacy of Formulations E and F. Formulation samples were inoculated with known levels of *A. niger* and sampled at predetermined intervals to determine if the system was capable of killing or inhibiting the propagation of organisms introduced into the products.

Formulations E and F are shown in the following table.

| | FORMULATION (wt %) | |
|---|---|---|
| INGREDIENT | E | F |
| Boric acid | 0.3 | 0.35 |
| Sodium borate | 0.11 | 0.11 |
| Mannitol | 0.85 | — |
| Sodium citrate | 0.56 | 0.56 |
| Citric acid | 0.021 | 0.21 |
| Sodium chloride | 0.48 | 0.48 |
| Pluronic P103 | 0.5 | 0.5 |
| Disodium edetate | 0.05 | 0.05 |
| Polyquad ® | 0.001 | 0.001 |
| NaOH and/or HCl | pH 7.0 | pH 7.0 |
| Purified water | q.s. | q.s. |

The results indicate that there was a 2.1 log reduction of *A. niger* with Formulation E and only 1.1 log reduction with Formulation F after 7 days. Formulation E met the BP standards for preservative efficacy against *A. niger*, while Formulation F failed to meet the BP standards.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. An aqueous ophthalmic solution comprising: 0.5 to 6.0 wt. % of a water soluble borate-polyol complex to enhance the antimicrobial activity of the solution, and water; wherein the borate-polyol complex comprises a borate compound selected from the group consisting of boric acid and pharmaceutically acceptable salts thereof and propylene glycol, and the molar ratio of borate to polyol is 1:0.1 to 1:10.

2. An aqueous ophthalmic solution according to claim 1, wherein the solution further comprises an effective amount of a viscosity-enhancing polymer.

3. An aqueous ophthalmic solution according to claim 2, wherein the viscosity-enhancing polymer comprises a cellulosic polymer.

4. An aqueous ophthalmic solution according to claim 3, wherein the cellulosic polymer comprises hydroxypropyl methylcellulose.

5. An aqueous ophthalmic solution according to claim 1, wherein the solution does not contain an ophthalmically acceptable antimicrobial agent.

6. An aqueous ophthalmic solution according to claim 1, wherein the solution contains the borate-polyol complex in an amount of 1.0 to 2.5 wt. %.

7. An aqueous ophthalmic solution according to claim 6, wherein the molar ratio of borate to polyol is 1:0.1 to 1:1.

8. An aqueous ophthalmic solution according to claim 6, wherein the molar ratio of borate to polyol is 1:0.25 to 1:2.5.

9. An aqueous ophthalmic solution according to claim 6, wherein the solution does not contain any ophthalmically acceptable antimicrobial agent.

10. An aqueous ophthalmic solution comprising: 0.5 to 6.0 wt. % of a water soluble borate-polyol complex to enhance the antimicrobial activity of the solution, and water; wherein the borate-polyol complex comprises a borate compound selected from the group consisting of boric acid and pharmaceutically salts thereof and sorbitol, and the molar ratio of borate to polyol is 1:0.1 to 1:10.

11. An aqueous ophthalmic solution according to claim 10, wherein the solution further comprises an effective amount of a viscosity-enhancing polymer.

12. An aqueous ophthalmic solution according to claim 11, wherein the viscosity-enhancing polymer comprises a cellulosic polymer.

13. An aqueous ophthalmic solution according to claim 12, wherein the cellulosic polymer comprises hydroxypropyl methylcellulose.

14. An aqueous ophthalmic solution according to claim 10, wherein the solution does not contain an ophthalmically acceptable antimicrobial agent.

15. An aqueous ophthalmic solution according to claim 10, wherein the solution contains the borate-polyol complex in an amount of 1.0 to 2.5 wt. %.

16. An aqueous ophthalmic solution according to claim 15, wherein the molar ratio of borate to polyol is 1:0.1 to 1:1.

17. An aqueous ophthalmic composition according to claim 15, wherein the molar ratio of borate to polyol is 1:0.25 to 1:2.5.

18. An aqueous ophthalmic solution according to claim 15, wherein the solution does not contain an ophthalmically acceptable antimicrobial agent.

* * * * *